(12) United States Patent
Niedrig et al.

(10) Patent No.: US 6,337,073 B1
(45) Date of Patent: Jan. 8, 2002

(54) INTRANASAL YELLOW FEVER VACCINATION

(75) Inventors: Matthias Niedrig, Berlin; Christiane Stahl-Hennig; Gerhard Hunsmann, both of Göttingen, all of (DE)

(73) Assignee: Deutsches Primatenzentrumg GmbH, Göttingen (DE)

( * ) Notice: Subject to any disclaimer, the term of this patent is extended or adjusted under 35 U.S.C. 154(b) by 0 days.

(21) Appl. No.: 09/581,218

(22) PCT Filed: Dec. 21, 1998

(86) PCT No.: PCT/EP98/08387

§ 371 Date: Jun. 22, 2000

§ 102(e) Date: Jun. 22, 2000

(87) PCT Pub. No.: WO99/32146

PCT Pub. Date: Jul. 1, 1999

(30) Foreign Application Priority Data

Dec. 22, 1997 (DE) ......................................... 197 57 301

(51) Int. Cl.[7] ........................ A01N 63/00; A61K 37/00
(52) U.S. Cl. ................. 424/218.1; 424/93.6; 435/235.1
(58) Field of Search ........................... 424/204.1, 218.1, 424/93.6; 435/235.1, 236, 237

(56) References Cited

U.S. PATENT DOCUMENTS 4,500,512 A    2/1985  Barme

FOREIGN PATENT DOCUMENTS

EP         0 877 086         11/1998

OTHER PUBLICATIONS

Gibson et al. "Effect of administration of sodium aurothiomalate on the virulence of yellow fever viruses in adult mice", Vaccine, vol. 8, No. 6 (Dec. 1990), pp. 590–594. QR189.V82.*

"Requirements for yellow fever vaccine (Requirements for Biological Substances No. 3, revised 1995)" WHO Technical Report Series, No. 872, 1998, pp. 30–50.

Jennings et al., "Analysis of yellow fever virus isolated from a fatal case of vaccine–associated human encephalitis", Journal of Infectious Diseases, vol. 169, No. 3, March 1994, pp. 512–518.

Barrett et al., "Comparison of neurovirulence of different strains of yellow fever virus in mice." Journal of General Virology, vol. 67, No. 4, April 1986, pp. 631–637.

Dunster et al., "Attenuation of virulence of flaviviruses following passage in HeLa cells.", Journal of General Virology, vol. 71, No. 3, March 1990, pp. 601–607.#jf139##

*Primary Examiner*—Jeffrey Stucker
(74) *Attorney, Agent, or Firm*—Arent Fox Kintner Plotkin & Kahn PLLC.

(57) ABSTRACT

The invention relates to vaccine preparations, pharmaceutical preparations and methods for inducing protective immunity in humans using a live, attenuated yellow fever virus of strain D17 preferably administered by an intranasal route of administration. The inventors have also developed an assay for detecting the induction of both the binding and neutralizing antibodies formed in a protective immune response in humans who have received an intranasal vaccine preparation of the kind described.

2 Claims, 1 Drawing Sheet

INTRANASAL YELLOW FEVER VACCINATION

Figure 1:
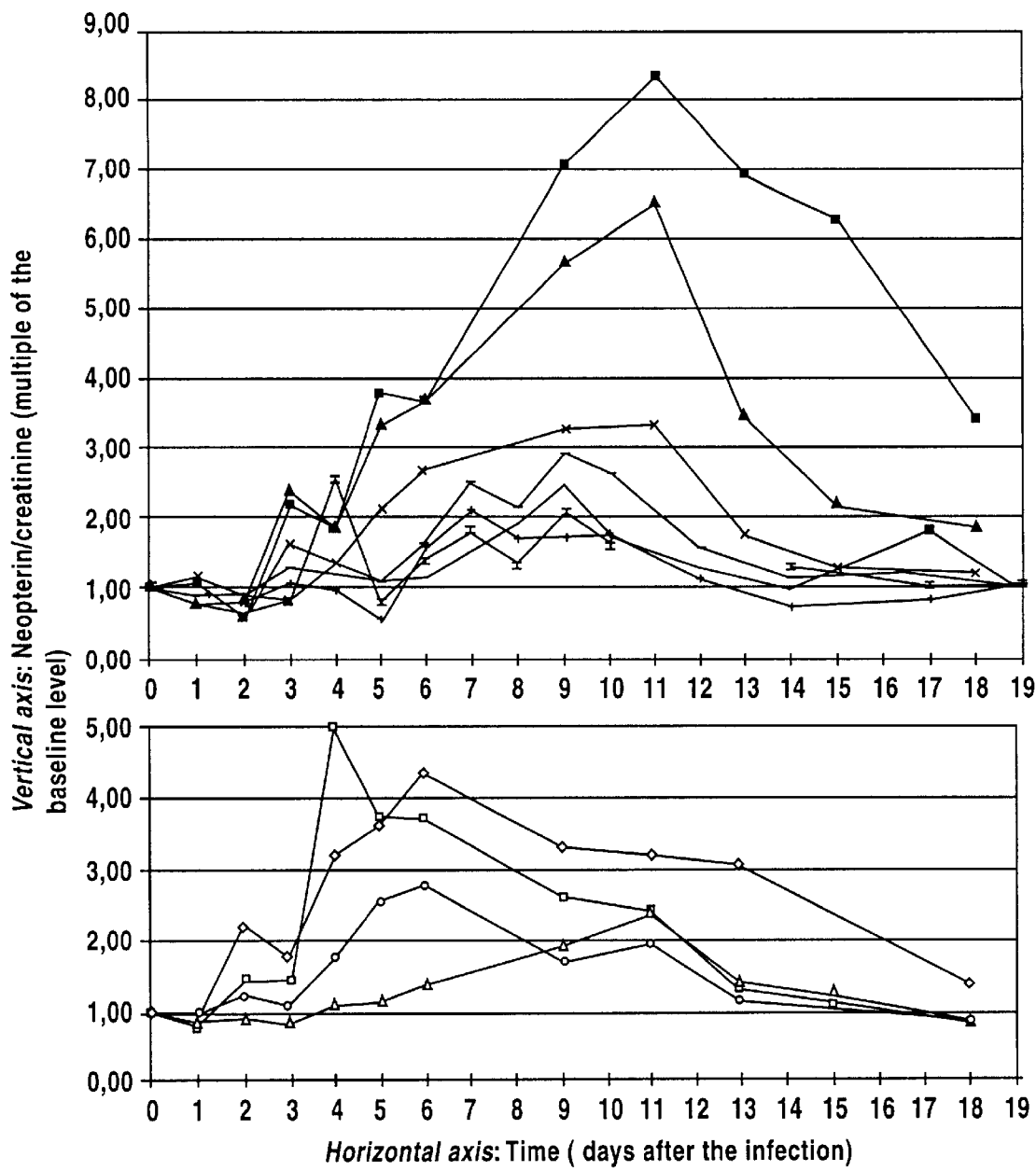

The invention relates to a medicament preparation for intranasal vaccination against yellow fever.

Yellow fever is a serious health problem in many areas of Africa and South America. Since the introduction of the live, attenuated 17D vaccine strain against yellow fever virus infection by Theiler in 1937 a very effective vaccine, which shows virtually no side effects, has been available against this infection (Theiler et al., J. Ex. Med. 65 (1937) 787–800). Prophylactic immunization with this active substance is very effective because immunity appears to persist life-long. However, because of incomplete vaccination of the population with 17D in endemic areas, yellow fever epidemics have occurred and still occur (Robertson et al., JAMA 276, No. 14 (1996) 1157–1162). This is connected in particular with the fact that the subcutaneous yellow fever vaccination used in the state of the art involves great expenditure and thus often cannot be employed comprehensively in many countries.

One object of the invention was therefore to provide a medicament preparation for vaccination against yellow fever which can be used in a simpler form than by subcutaneous injection.

This object is achieved according to the invention by a medicament preparation for intranasal vaccination against yellow fever.

It has been found in this connection that on intranasal administration of a vaccine against yellow fever it is possible to achieve an effective immune response leading to the expectation of reliable vaccine protection.

It is possible by administering an active substance against yellow fever through the nose to obtain reliable vaccine protection which is not inferior to the vaccine protection to be achieved by subcutaneous vaccination. In contrast to this, no immune response leading to the expectation of reliable vaccine protection is achieved with other administration routes such as, for example, oral or gastrointestinal. Intranasal vaccination makes economic administration possible, which makes possible general vaccination which is simple to perform, and is thus suitable in particular for mass immunizations.

The medicament preparation according to the invention preferably comprises as active substance the yellow fever vaccine strain 17D, in particular a live, attenuated 17D yellow fever vaccine complying with the stipulations of the World Health Organization (Barry et al., "Requirements for Yellow Fever Vaccine", WHO Technical Report Series, No. 594 (1976) 34–35). A single vaccine dose preferably contains at least $10^3$ plaque-forming units (PFU).

The active substance is preferably introduced into a solvent suitable for intranasal administration. Examples of suitable solvents are physiological salt solutions such as, for example, a 0.9% strength sodium chloride solution. The active substance is preferably dissolved in the salt solution, for example sodium chloride solution, immediately before use. Other suitable solvents are distilled water and heavy water ($D_2O$), with each of which excellent stabilization of the vaccine can be achieved. The medicament preparation according to the invention may additionally comprise other pharmaceutically suitable solvents and/or excipients. The solvent is employed in particular for dissolving and administering freeze-dried 17D vaccine.

A further aspect of the invention is the use of a medicament preparation which comprises as active substance the yellow fever vaccine strain 17D for intranasal vaccination against yellow fever. A live, attenuated 17D vaccine strain is preferably used. It has been found, surprisingly, that on administration of the active substance through the nose it is possible to achieve a reliable immune response leading to the expectation of reliable vaccine protection.

The invention further comprises the use of an active substance comprising the yellow fever vaccine strain 17D for producing a medicament for intranasal vaccination against yellow fever.

The invention is explained further by the following examples and by FIG. 1.

FIG. 1 shows neopterin/creatinine levels in monkeys vaccinated intranasally, perorally and subcutaneously, depicted as multiple of the baseline level (level before vaccination). Black symbols refer to monkeys positive in the virus isolation and vaccinated intranasally or perorally (+=8488, ■=1655, Δ=1635, ↑=1637, ◊=1863, --=1889, x=1891; the numbers in each case indicate the identification number of the experimental animal). The white symbols refer to the four monkeys immunized subcutaneously as controls (=8482, ◊=8493, Δ=8494, ○=8495), whose levels are shown in the lower diagram.

Example 1

Vaccination of Rhesus Monkeys (*Macaca mulatta*)

Four groups of 4 to 6 rhesus monkeys were in each case vaccinated with the live attenuated yellow fever vaccine strain 17D. The animal model used for immunization of humans with a yellow fever vaccine comprised young and adult rhesus monkeys (*Macaca mulatta*) with a body weight between 3 and 7 kg. Six adult monkeys were chosen, because the wings of their noses were larger, for the intranasal administration of vaccine, so that conventional spray devices could be used. The other three groups comprised 4 young monkeys in each case. All the monkeys were housed in separate cages. Blood samples were taken under ketamine anesthesia one week before the vaccination and on days 2, 4, 6, 14, 28 and about 130 after the vaccination (p.v.). All the sera were stored in aliquots at −70° C. until used. For measurement of the neopterin content, urine samples were collected each day between day 1 and day 10 after the vaccination, and at 2-day intervals up to day 19.

The active substance used was a live, attenuated 17D yellow fever vaccine (Lot No.: 142/94/1) which had been produced at the Robert-Koch-Institut, Berlin, Germany in accordance with the stipulations of the WHO (Barry et al., Requirements for Yellow Fever Vaccine, WHO Technical Report Series, No. 594 (1976) 34–35). A single vaccine dose contained at least 6.8×104 plaque-forming units (PFU) and was dissolved in an appropriate volume of a 0.9% strength sodium chloride solution immediately before use.

The vaccine was administered using a spray device into each wing of the nose in a first group of six animals.

A 17D vaccine dose was introduced by oral spray administration with a spray device (130 μl per puff) directly into the throat of a second group. In this case, three puffs, equivalent to a human dose, were introduced. This administration route is referred to as the peroral route herein.

The 17D vaccine was administered in capsules via the gastrointestinal route to a third group of monkeys. For this purpose, the vaccine was packed into gelatin capsules and coated with an acid-stable cellulose coating. The capsules were tested for their acid stability by incubation with 0.1 N HCl at 37° C. for 24 hours. In order to prevent the animals damaging the capsules by biting, the capsules were introduced directly into the stomach using a tube of suitable size.

A fourth group consisting of four other monkeys served as positive control. These animals received subcutaneous administration of the 17D vaccine dissolved in 0.5 ml of 0.9% strength sodium chloride solution.

After the vaccination, the progress of the viremia induced by the 17D vaccine strain was followed by the quantitative plaque assay on the serum taken on the fourth and sixth day after the vaccination. The assay was carried out in accordance with the instructions of De Madrid et al., A simple micro-culture method for the study of group B arboviruses, Bulletin of the World Health Organization 40, (1969) 113–121. The results are shown in Table 1. The development of antibodies specific for yellow fever virus was determined by an immunofluorescence assay (IFA) and by a neutralization assay as described below.

the serum were mixed with a guanidine othiocyanate lysis buffer and with size-fractionated silica particles. After incubation at room temperature for 10 minutes, the solution was mixed and centrifuged. The silica-nucleic acid pellet was washed twice with 1 ml of washing buffer, twice with 1 ml of 70% ethanol and once with 1 ml of acetone. The pellet was left to dry in a heating block. The nucleic acids were eluted by adding 70 $\mu$l of a TE buffer to the pellet. The suspension was thoroughly mixed and again incubated. After a centrifugation, 50 $\mu$l of the RNA-containing supernatant were extracted. Previously published flavivirus-specific primers were used for the first run of a nested PCR, followed by a nested PCR with a newly developed, specific primer (CAC Aag TgA ATT Tgg Cg), (Eldadah et al., J. Med Virol. 33 (1991) 260–267).

TABLE 1

Detection of a 17D yellow fever infection in rhesus monkeys on immunization by various routes

| Monkey group[a] | Animal No. | 17D virus detection on post-vaccination day[b] | | IgM | | IgG | | Neutralizing antibody titer post-vaccination day[d] | | |
|---|---|---|---|---|---|---|---|---|---|---|
| | | 4 | 6 | 14 | 28 | 14 | 28 | 130 | 14 | 28 | 130 |
| Group 1 | 1655 | 57/+ | 7/+ | 1:40 | 1:320 | 1:640 | 1:1280 | 1:80 | 1:10 | 1:50 | 1:200 |
| Intranasal | 1635 | 7/+ | 78/+ | 1:160 | 1:160 | 1:640 | 1:2560 | 1:320 | 1:10 | 1:20 | 1:200 |
| | 1637 | 57/+ | 1143/+ | 1:160 | 1:10 | 1:320 | 1:2560 | 1:640 | 1:10 | 1:20 | >1:320 |
| | 1863 | 0/+ | 8/+ | 1:10 | 1:10 | 1:40 | 1:80 | 1:40 | 1:50 | 1:10 | 1:90 |
| | 1889 | 0/– | 0/– | 1:10 | 1:10 | 1:40 | 1:320 | 1:20 | 1:60 | 1:10 | 1:80 |
| | 1891 | 0/+ | 0/+ | 1:20 | 1:10 | 1:320 | 1:320 | 1:20 | 1:50 | 1:20 | 1:50 |
| Group 2 | 8478 | 0/– | 0/– | n.t. | n.t. | — | — | n.t. | — | — | — |
| Peroral | 8484 | 0/– | 0/– | n.t. | n.t. | — | — | n.t. | — | — | — |
| | 8486 | 0/– | 0/– | n.t. | n.t. | — | — | n.t. | — | — | — |
| | 8488 | 36+ | 7+ | 1:10 | 1:10 | 1:320 | 1:320 | n.t. | 1:10 | 1:30 | n.t. |
| Group 3 | 8479 | 0/n.t. | 0/n.t. | n.t. | n.t. | <1:10 | <1:10 | n.t. | <1:10 | <1:10 | n.t. |
| Gastrointestinal, | 8480 | 0/n.t. | 0/n.t. | n.t. | n.t. | <1:10 | <1:10 | n.t. | <1:10 | <1:10 | n.t. |
| capsule | 8483 | 0/n.t. | 0/n.t. | n.t. | n.t. | <1:10 | <1:10 | n.t. | <1:10 | <1:10 | n.t. |
| | 8487 | 0/n.t. | 0/n.t. | n.t. | n.t. | <1:10 | <1:10 | n.t. | <1:10 | <1:10 | n.t. |
| Group 4 | 8482 | 7/+ | 0/+ | 1:20 | 1:10 | 1:320 | 1:320 | 1:40 | 1:10 | 1:30 | 1:220 |
| Subcutaneous | 8493 | 100/+ | 0/+ | 1:20 | <1:10 | 1:1280 | 1:640 | 1:40 | 1:10 | 1:30 | 1:160 |
| | 8494 | 29/+ | 129/+ | <1:10 | 1:20 | <1:10 | 1:640 | 1:20 | 1:10 | 1:30 | 1:140 |
| | 8495 | 36/+ | 0/+ | 1:20 | <1:10 | 1:640 | 1:1280 | 1:40 | 1:10 | 1:100 | 1:220 |

[a]Macaca mulatta;
[b]the number refers to the number of plaques per ml of serum (PFU/ml), + = positive result in RT-PCR, – = negative result in RT-PCR;
[c]1:x = reciprocal titer in IF,
[d]reciprocal titer in 90% plaque reduction neutralization assay [PFU/ml], <1:10 = no reaction, n.t. = not tested The yellow fever vaccination was accepted well by all the monkeys overall and no side effects were observed. On intranasal administration of the vaccine, all six monkeys were productively infected, as was shown by the detection of virus-specific antibodies. In contrast to this, on use of the peroral vaccination route only one of four animals (animal No. 8488) showed signs of infection with 17D. On gastrointestinal administration of the vaccine, none of the four animals developed signs of a yellow fever infection. The four monkeys in the positive control group which had received subcutaneous injection of the vaccine strain by contrast showed a clear humoral immune response to the yellow fever virus. In almost all the animals which formed virus-specific antibodies against 17D and thus indicated successful vaccination the 17D virus was isolated by a plaque assay or the viral RNA was detected on days 4 and 6 after the vaccination.

RNA for the RT/PCR was extracted by a modified form of the procedure previously described by Boom et al. (Boom et al., J. Clin. Microbiol 28 (1990) 495–503). For this, 50 $\mu$l of Most of the yellow fever vaccines commonly used induce a strong T-helper cell-dependent neutralizing antibody response after one vaccination with live 17D viruses in order to combat possible wild-type yellow fever infections. This fact has been investigated and demonstrated by several groups (see, for example, Smithburn et al., Am. J. Trop. Med. 25 (1945) 217–223; Hill et al. J. General Virol. 73 (1992) 1115–1123; Monath, Yellow fever vaccines: the success of empiricism, pitfalls of application and transition to molecular vaccinology, ed. S. Plotkin & B. Fantini, Vaccinia, vaccination and vaccinology: Jenner, Pasteur and their successors, Elsevier, Paris, 1996, pages 157–182). For this reason, the formation of binding and neutralizing antibodies against the 17D vaccine strain was investigated.

The immunofluorescence assay for 17D-specific IgM and IgG was carried out with 17D-infected PS cells which correspond to the state of the art. 17D-infected VeroB4 cells are placed on slides and fixed with acetone. The fixed cells are covered with a serum dilution (1:10, 1:20, etc.) in phosphate buffer pH 7.2, and incubated at 37° C. for one hour. Unbound antibodies are removed by washing the slides three times. This is followed by specific labeling with the fluorescent dye-coupled detection antibody (for example anti-human IgG FITC). After a further three washing steps, the preparation is dried and can be assessed under a fluorescence microscope. Highly fluorescent regions in the 17D-infected cells demonstrate specific antibodies directed against 17D structural proteins.

Uninfected PS cells were used as negative controls. Before the vaccination, no specific anti-17D IgM or anti-17D IgG antibodies were detected in the animals. Within two weeks after the 17D yellow fever vaccination it was possible to detect high concentrations of specific anti-17D IgM antibodies in successfully vaccinated animals with titers between 1:10 and 1:160, which either remained constant or decreased over the course of 2 weeks. It was additionally possible to show the presence of specific anti-17D IgG antibodies for these animals on days. 14 and 28 after the vaccination, with maximum titers between 1;80 and 1:2560. Six months after the immunization, all the successfully vaccinated animals had constant IgG titers between 1:20 and 1:640.

In addition, neopterin, a molecule which is released by monocytes/macrophages, in particular after viral stimulation, was analyzed in the serum and in the urine of all the animals by the procedure of Huber et al. (Huber et al., J. Exp. Med. 160, (1994) 310–316). A commercially available assay (Brahms Diagnostica GmbH, Berlin, Germany) was used in accordance with the manufacturer's instructions to detect neopterin in the serum. The neopterin level in the urine was analyzed as previously described (Fendrich et al., AIDS 3 (1989) 305–307) . In order to adjust the neopterin levels to the differences in the urine specific gravity, the levels were related to the creatinine concentrations. Because of differences in the individual base line levels of neopterin, the concentrations obtained after the vaccination were additionally related to the levels before the vaccination and expressed as a multiple of the respective base line levels. It was possible to show in parallel with the viremia a distinct increase in neopterin for all 17D virus-infected animals (ct. FIG. 1). The serum neopterin concentrations determined in three intranasally vaccinated monkeys (Nos. 1655, 1636 and 1637) showed peaks on day 6 after vaccination, with concentrations between 8 and 12.5 nm/ml. This peak was followed by a slow decline in serum neopterin. The levels measured on day 18/19 after the vaccination were similar to the levels before the vaccination. For the subcutaneously vaccinated animals there was observed to be a distinct rise in serum neopterin on day 2 after the vaccination, which lasted up to day 6 for animals 8482 and 8495 with a content of up to 16 ng/ml. In general, it can be stated that the neopterin contents in blood and serum correspond to one another, with only very small differences occurring over time.

The neutralization plaque reduction assay was carried out as described previously on PS cells (De Madrid et al., A simple micro-culture method for the study of group B arboviruses, Bulletin of the World Health Organization 40 (1969) 113–121). Briefly summarized, two-fold dilutions of the monkey sera in the range from 1:20 to 1:320 were mixed with dose units of 100 plaque-forming units culture infectivity of a 17D virus reference preparation (applicant's lot No. 354/1). After incubation at 37° C. for 1 hour, 0.2 ml of this mixture was added to the same volume of a PS cell suspension containing $6 \times 10^5$ cells/ml. A 1.6% strength CMC/L-15 solution (BDH Chemicals Ltd., U.K.) supplemented with 3% FCS (fetal calf serum) was used to overlay after incubation for 4 hours. The cultures were kept at 37° C. for 5 days. The cells were then washed with PBS and fixed with a 10% strength formaldehyde solution for 10 minutes. Naphthalene black was used to stain the cell layers, the plaques were counted, and the reciprocal titer of 90% neutralization was calculated. All the animals responding to the vaccination developed a neutralization titer in the range from 1:10 to 1:100 within 4 weeks after the vaccination and high titers between 1:80 and 1:320 after 4 months. It was possible in this way to obtain a reliable and long-lasting vaccine protection with intranasal administration of the vaccine too. As has been shown in human vaccine trials, titers of neutralizing antibodies persist for at least 10 years after a first vaccination (Rosenzweig et al. Am. J. Trop. Med. Hyg. 12 (1963) 230–235; Poland et al., Persistence of neutralizing antibody 30–35 years after immunization with 17D yellow fever vaccine, Bulletin of the World Health Organization 59(6) (1981) 895–900).

In contrast to intranasal administration, only one of four animals with peroral administration of the vaccine showed a distinct response to 17D. This route is thus unsuitable for 17D vaccination. On the other hand, intranasal spray administration surprisingly afforded successful vaccination for all six monkeys tested. Gastrointestinal administration of an encapsulated 17D vaccine did not lead to any infection of the test animals either, so that no vaccine protection can be achieved through this administration route either.

In summary, it can be stated that intranasal administration of a live, attenuated 17D vaccine can effectively induce protective immunity. Intranasal use of a 17D vaccine thus represents a suitable and economically interesting alternative for mass vaccinations in the affected countries, in particular because injections with vaccination guns are associated with a high risk of transmitting hepatitis B (Abb et al., J. Infect. Diseases 144 No. 2 (1981) 179; Brink et al., J. Med. Microbiol. 20 (1985) 393–397, Shah et al., Morbidity and Mortality Weekly Report 35, No. 23 (1986) , 373–376).

What is claimed is:

1. A method for inducing protective immunity against yellow fever virus in a human subject, comprising administering intranasally a live, attenuated yellow fever virus to a human subject wherein the live, attenuated yellow fever virus is administered to the subject in an amount effective for inducing a binding and a neutralizing antibody response.

2. The method according to claim 1, wherein the amount is at least $10^3$ plaque-forming units of the yellow fever virus.

* * * * *